United States Patent [19]
Wittkopp et al.

[11] 3,986,034
[45] Oct. 12, 1976

[54] X-RAY EXAMINATION APPARATUS

[75] Inventors: Fritz Wittkopp, Weiher; Gerhard Wenzek, Erlangen, both of Germany

[73] Assignee: Siemens Aktiengesellschaft, Erlangen, Germany

[22] Filed: Mar. 19, 1975

[21] Appl. No.: 559,873

[30] Foreign Application Priority Data
Mar. 29, 1974 Germany............................ 2415410

[52] U.S. Cl. ................................................. 250/468
[51] Int. Cl.² ......................................... G03B 41/16
[58] Field of Search ........... 250/505, 511, 512, 513, 250/468

[56] References Cited
UNITED STATES PATENTS

| | | | |
|---|---|---|---|
| 3,502,878 | 3/1970 | Stewart | 250/512 |
| 3,518,435 | 6/1970 | Kok | 250/511 |
| 3,581,094 | 5/1971 | Peyser | 250/511 |
| 3,829,698 | 8/1974 | Goetz | 250/511 |

*Primary Examiner*—Craig E. Church
*Attorney, Agent, or Firm*—Haseltine, Lake & Waters

[57] ABSTRACT

An X-ray examination apparatus including an examination table, an X-ray source having remote-controllable focusing means for the X-radiation, a cassette drawer which is insertable below the patient's support platform of the examination table, including clamping means for the X-ray film cassette, and means for converting the cassette dimensions which are determined by the clamping means into electrical values for effecting the control of the focusing means.

1 Claim, 2 Drawing Figures

X-RAY EXAMINATION APPARATUS

FIELD OF THE INVENTION

The present invention relates to an X-ray examination apparatus including an examination table, an X-ray source having remote-controllable focusing means for the X-radiation, a cassette drawer which is insertable below the patient's support platform of the examination table, including clamping means for the X-ray film cassette, and means for converting the cassette dimensions which are determined by the clamping means into electrical values for effecting the control of the focusing means.

DISCUSSION OF THE PRIOR ART

A control installation for confining the utilizable X-ray beam of an X-ray tube is known wherein, upon the insertion of an X-ray film cassette into the cassette retainer of an X-ray examination apparatus, two continually variable measurement value transducers in the cassette retainer may be adjusted through displacement of the clamping jaws. One of the measurement value transducers is adjusted by means of the clamping jaws determining or sensing the width of the cassette, and the other measurement value transducer by the clamping jaws determining or sensing the length of the cassette. These two measurement value transducers are connected to a control circuit, through the intermediary of which the usable X-ray beam is then adjusted pursuant to the cassette dimensions sensed by the clamping jaws of the cassette retainer. However, in this control installation, the extensive and complex control requirements, as well as the electrical connection of the otherwise loosely insertable and withdrawable, and also removable cassette retainer, has been found to be disadvantageous.

SUMMARY OF THE INVENTION

Accordingly, it is an object of the present invention to develop a cassette drawer including an arrangement for the control of the focusing means in dependence upon the dimensions of the inserted X-ray film cassette, which is self-sufficient without any thereabout suspended electrical cable, and is thereby readily removable from the examination table when, for example, there is required the insertion of a film plate changer, a series exposure arrangement, or a picture amplifier-video installation below the examination table. In an X-ray examination apparatus of the above-mentioned type, a clamping jaw is inventively coupled with a transmitter, the latter of which is slidably supported in the cassette drawer transverse to the direction of insertion of the cassette drawer into the examination table, and with switch means being provided in the examination table which are adapted to be actuated by the transmitter upon the cassette drawer being inserted into the examination table, and which are associated with distinct positions of the transmitter in conformance with the different cassette dimensions of the cassettes which are insertable into the cassette drawer. Thereby is achieved that the switch means, and consequently also the electrical control cable, first begin in the stationary portion of the examination table, and that the cassette drawer may be constructed without the necessity for electrical connections. This allows the cassette drawer to be readily withdrawn from the examination table in case of need, and to be located elsewhere.

The construction of the cassette drawer may be rendered particularly simple when, in a suitable embodiment of the invention, the clamping jaw is coupled with the transmitter through a spring-loaded traction cord. A traction cord allows itself to be particularly easily guided interiorly of a cassette drawer and is, moreover, a dependable and inexpensive adjusting means.

A similarly inexpensive, as well as dependable construction is obtained when the clamping jaw, in a further particularly advantageous embodiment of the invention, is connected to the transmitter for determining the cassette width, as well as also the cassette length, through the intermediary connection of a lever which is articulated to the clamping jaw and connected to the transmitter, and wherein the lever is provided with projections for the sensing of the dimensions of the cassettes which are insertable into cassette drawer in the longitudinal direction of the clamping jaw. As a result of the interposition of the lever, further distinct positions of the transmitter are produced due to the second dimension of the cassette. This leads to that this lever eliminates the need for a further transmitter with the therewith associated adjusting elements.

In a further particularly advantageous embodiment of the invention, there may be employed a permanent magnet as the transmitter, and magnetically actuatable contacts as the switch means, in effect, so-called reed contacts. This has the advantage that the transmitter may remain in the cassette drawer without requiring any supply conduit, and the switching of the focusing means may be carried out in a completely contactless manner from the cassette drawer.

BRIEF DESCRIPTION OF THE DRAWINGS

Further details of the invention may now be ascertained from the following detailed description of exemplary embodiments thereof, taken in conjunction with the accompanying drawings; in which.

DETAILED DESCRIPTION

Figure 1:
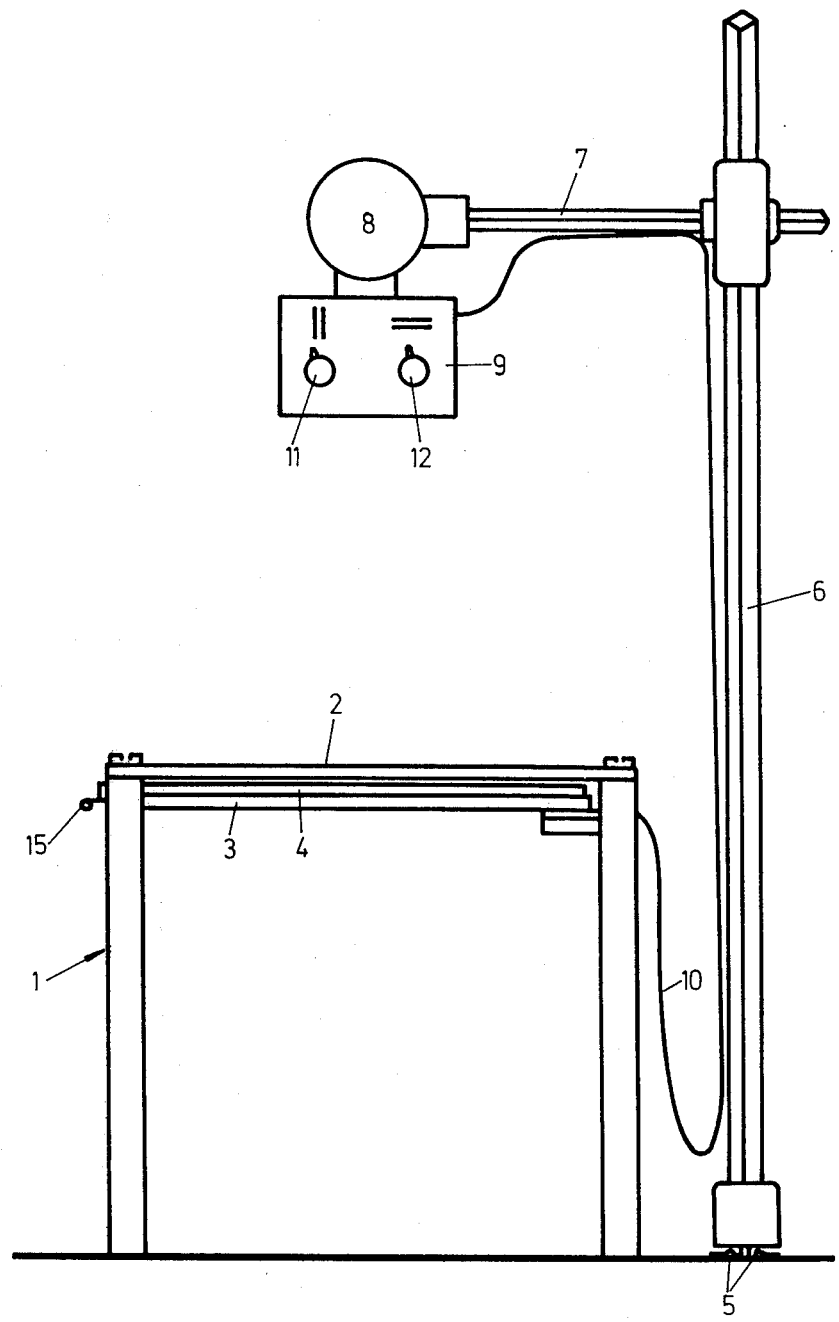
FIG. 1 shows a side elevational view of an X-ray examination apparatus having a cassette drawer pursuant to the invention.

Referring now in detail to the drawings, in FIG. 1 there may be recognized an examination table 1 having a patient support platform 2, and a cassette drawer 4 which is insertable, below the patient support platform, in a frame 3 movable along the longitudinal direction of the table. Adjacent the examination table 1 there may be ascertained a support column 6 which is movable on a rail 5 along the floor, and which carries an X-ray tube 8 and an X-ray diaphragm suspended from horizontal support arm 7. The X-ray diaphragm is connected with the examination table 1 through an electrical cable 10. The diaphragm is manually adjustable with the aid of the setting knobs 11, 12. These setting knobs, however, have remote-controllable setting means (not shown) associated therewith, by means of which the X-ray diaphragm may be adjusted in an electrical mode.

Figure 2:
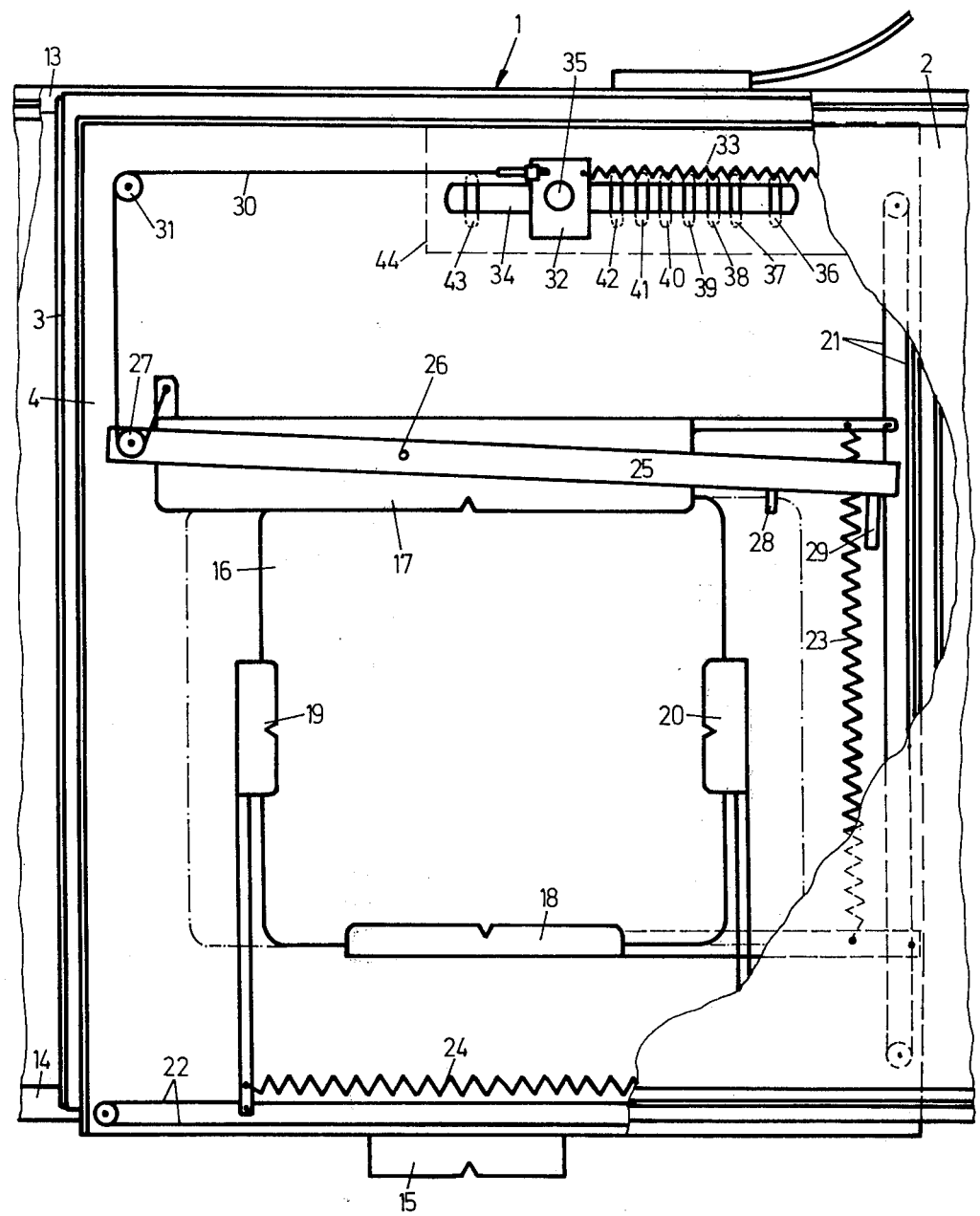
FIG. 2 is a plan view of the examination table, with the patient support platform shown broken away for purposes of clarity.

The examination table 1 may be seen in FIG. 2 in plan view. In that view, in which the patient support platform 2 has been broken away for purposes of clarity, there may be recognized spars, 13, 14 of the examination table, along which there are movable the frames 3 for the insertion of the cassette drawer 4. The cassette drawer 4, which is provided with a handle 15, has clamped therein an X-ray film cassette 16 between the clamping jaws 17, 18, 19 and 20. The clamping jaws are pairwise mutually adjustable opposite each other, in the usual manner, through the use of traction cords 21, 22, so as to centrally clamp the cassette 16 irrespective of the latters' configuration. The clamping jaws are pressed against the cassette by means of springs 23, 24. Supported on one of the clamping jaws 17 is a two-armed lever 25 so as to be pivotable about an axis 26 which is oriented in perpendicular to the plane of the cassette drawer 4. This lever is provided on one side thereof with a cord sheave 27 and, on the oppositely located side, carries two projections 28, 29 of which the outer projection is longer than the inner projection. These projections are located at such distances from the axis 26 of the lever 25 whereby the inner projection 28 may come into contact only with cassettes of medium widths, and the longer outer projection 25 only with cassettes having the largest possible width. From the clamping jaw 17 which is carried by the lever 25, a traction cord 30 is conveyed along the rear edge of the cassette drawer over the cord sheave 27 which is supported on the lever, and over a further traction cord-angling sheave 31, and with its other end is fastened to a tension spring 33 which is hooked into the cassette drawer through the interposition of a small plate 32. Along the path, which is traversed by the plate 32 within the cassette drawer 4 in dependence upon the tension of spring 33, a slot 34 is formed in the surface of the cassette drawer. Onto this plate 32 there is fastened a permanent magnet 35. Through the slot 34 in the surface of the cassette drawer, across which the permanent magnet 35 is slidable, there may be recognized reed contacts 36, 37, 38, 39, 40, 41, 42, 43, which are mounted on a plate 44 shown in chain-dotted relationship, and which is fastened to the examination table. These reed contacts, which are not connected with the cassette drawer 4, are connected through a cable 10 with the setting means for the focusing diaphragm 9 on the X-ray tube 8.

For effecting the insertion of an X-ray film cassette 16, the cassette drawer 4 is pulled forwardly from below the examination table 1 by means of the handle 15. The X-ray film cassette 16 is then positioned between the clamping jaws 17, 18, 19, 20 which place themselves on all sides of the X-ray film cassette through the spring force, and center the latter at the center point of the cassette drawer. Through the dimensions of the cassette 16 there is determined the distance of the clamping jaws from the center of the cassette drawer. The position of the upper clamping jaws 17 is transmitted to the traction cord 30. The latter then is displaced along the slot 34 in the cassette drawer 4 against the force of spring 33 so as to take along the plate 32 with the permanent magnets 35 in conformance with the position of the clamping jaws in the cassette drawer. If an equally high, but wider X-ray film cassette (shown in FIG. 2 in chain-dotted illustration) is inserted between the clamping jaws, then effectively the upper clamping jaw 17 remains in the same positon as shown in FIG. 2, however, this wider X-ray film cassette, in accordance with its width, will press back either the inner or even the outer longer projection 28 or 29 of the lever 25 which is articulated on the clamping jaw. Consequently, the lever 25 will be further rotated with respect to the position shown in FIG. 2 against the clockwise direction. The traction cord will now be conveyed about a larger path about the sheave 27 which is supported on the lever 25, so that the permanent magnet 35 is displaced for a greater distance as compared to the insertion of an equally high, but smaller X-ray film cassette. This new position of the permanent magnet 35, however, has a new reed contact 36 through 43 associated therewith. In this manner, the usual different commercial widths of X-ray film cassettes may be scanned independently of their height, without requiring a further transmitter or further setting means which would need to be adjusted from the side clamping jaws 19 and 20. As soon as the cassette drawer 4 is inserted in its exposure position below the X-ray support platform 2, the permanent magnet 35 is located above the reed contacts of the examination table. In accordance with the position of the permanent magnet in the X-ray drawer, a completely determinate reed contact is actuated in conformance with the dimensions of the inserted X-ray film cassette. Hereby, not only particular electrical values can be preset, which will set a follower control into operation through the intermediary of electrical measurement converters, but also completely particular power circuits, respectively, stop switches may be actuated which, in the simplest manner, will switch off the motors in the X-ray focusing diaphragm after reaching a new focusing position. Thereby, the construction of the remote control becomes substantially simpler and much less expensive to manufacture. If the X-ray drawer 4 is not required, or if it will cause a disturbance below the examination table, when, for example, a picture amplifier - video installation is to be inserted, then it may be simply pulled out by means of the handle 15, without the need for any previous separation of cables.

It is also conceivable that within the table frame there may be rigidly built in other types of transmitters such as, for example, signal lamps, and to merely locate a reflector on the plate in the cassette drawer, which transmits the signals of the transmitter to a measurement sensor which is located in the cable frame, such, as for example, photo cells. Also in this instance, any cable leading to the cassette drawer, in addition to any therewith associated contact or plug units, becomes superfluous.

The transmitter may also be constituted of cam plates, and the contacts adapted to be actuated in response to contacting the cam plates.

While there has been shown what is considered to be the preferred embodiment of the invention, it will be obvious that modifications may be made which come within the scope of the disclosure of the specification.

What is claimed is:

1. In an X-ray examination apparatus including an examination table with a patients' support platform; an X-ray source having remote-controllable focusing means for the X-radiation; a cassette drawer adapted to be inserted below said patients' support platform of said examination table; clamping means for clamping an X-ray film cassette within said cassette drawer; and means for converting the cassette dimensions determined by said clamping means into electrical values for the control of said focusing means, the improvement comprising: said clamping means including at least one clamping jaw; a transmitter being located in said cassette drawer slidably supported in a direction transverse to the insert direction of said cassette drawer into said examination table, said clamping jaw being coupled to said transmitter; switch means in said examination table adapted to be actuated by said transmitter upon insertion of the cassette drawer into said examination table, said switch means being associated with distinct positions of said transmitter pursuant to the different cassette dimensions of the cassettes which are insertable into said cassette drawer; a spring-loaded traction cord for coupling said clamping jaw to said transmitter; a lever articulated to said clamping jaw being interposed for connecting said clamping jaw with said transmitter for having said clamping jaw contact the cassette width and the cassette length; and projections on said lever for sensing the dimensions of the cassettes insertable into said cassette drawer in the longitudinal direction of said clamping jaw; said transmitter comprising a permanent magnet, and said switch means comprising magnetically actuatable contacts; said contacts being reed contacts; frame means for holding said cassette drawer; means for converting the dimensions sensed into movement transverse to the insertion direction of the cassette drawer into said frame means, the correct responsive switch contact being actuated even with incomplete insertion of the cassette drawer into said frame means.

* * * * *